United States Patent [19]

Dettman

[11] Patent Number: 4,816,223
[45] Date of Patent: Mar. 28, 1989

[54] STERILIZATION OF ASCORBATES

[76] Inventor: Ian C. Dettman, 9 Rogers St., Mentone, Victoria 3194, Australia

[21] Appl. No.: 65,520

[22] Filed: Jun. 23, 1987

[30] Foreign Application Priority Data

Jun. 23, 1986 [AU] Australia .............................. PH6524

[51] Int. Cl.$^4$ ........................... A61L 2/08; A61L 2/12; A61L 2/20
[52] U.S. Cl. ......................................... 422/28; 422/21
[58] Field of Search ....................... 422/21, 28, 26, 27, 422/41

[56] References Cited

U.S. PATENT DOCUMENTS

| | | | |
|---|---|---|---|
| 4,058,213 | 11/1977 | Stone | 53/431 |
| 4,447,399 | 5/1984 | Runnells et al. | 422/27 |
| 4,647,458 | 3/1987 | Ueno et al. | 422/28 |

FOREIGN PATENT DOCUMENTS 514503  7/1977  Australia .

Primary Examiner—Barry S. Richman
Assistant Examiner—Lyle Alfandary-Alexander
Attorney, Agent, or Firm—Merchant, Gould, Smith, Edell, Welter & Schmidt

[57] ABSTRACT

A method of treating biologically affective particulate material includes adding absolute ethyl alcohol to the particulate material and heating for sufficient time to kill organisms present, but insufficient time to cause breakdown of particulate material. The method is particularly adapted for the treating of sodium ascorbate, a heat sensitive material. Preferably absolute ethyl alcohol is used, to help minimize the presence of water, which can cause decomposition of the sodium ascorbate. In preferred applications, heating is to a temperature within the range 100°–130° C., and for heating cycles of no greater than about 2–10 minutes, with a cooling interval between successive heating cycles.

7 Claims, No Drawings

STERILIZATION OF ASCORBATES

This invention relates to the treating of biologically affective particulate material, and to an improved form for storage of such material.

The term "biologically affective particulate material" as used herein denotes particulate solid material which is nonreactive with ethyl alcohol and which is suitable to be administered, such as mixed with a suitable liquid carrier and administered by injection, to humans or animals.

Australian Pat. specification No. 514503 discloses a method of providing biologically active particulate material. In that method, a charge of the material is placed in a sealable container and contacted therein with an amount of ethyl alcohol sufficient to produce a sterilizing ethyl alcohol vapour but insufficient to cause visible wetting of the material. The container then is sealed and stored for a time sufficient to enable the vapour to sterilize the material.

The method of Australian Pat. No. 514503 is particularly applicable to the sterilization of ascorbates, such as sodium ascorbate. While the method has formed acceptance in providing a suitable source of sterile ascorbate for use in producing sterile solutions for injection, it is thought the method may not always be lethal to some spore forming organisms, such as Bacillus.

The present invention is directed to providing an improved method of treating biologically affective particulate material.

The invention provides a method of treating a biologically affective particulate material, wherein said material is subjected to the sterilizing action of ethyl alcohol and also is heated; the material being heated to a temperature and for a time sufficient to kill organisms present but insufficient to cause significant breakdown of the material.

Most conveniently the heating is performed after the material is in contact with the alcohol, and preferably after sealing a container to which the material and alcohol has been charged. However, while less desirable, sealing of the container can be performed after heating.

The amount of alcohol preferably is such as to maintain a sterilizing alcohol vapour in the sealed container at ambient temperatures, but insufficient to cause visible wetting of the material. However, where the container is sealed after heating, a greater amount of alcohol can be used, with part of this being driven off during heating and thereby substantially purging the container of other gases. Such practice generally is not suitable with small containers due to the likelihood of substantially all of the alcohol being driven off during heating; but it can be appropriate with larger containers enabling control over gas flow from the container during heating.

It long has been held that biologically affective particulate materials, such as ascorbates can not be exposed to heat for sterilizing purposes, due to the tendency of such materials to decompose. Ascorbates therefore have not been subjected to conventional sterilization procedures involving heat sufficient to kill organisms present. However, this belief appears to stem from an awareness of the decomposition of Vitamin C during cooking of foodstuffs but, contrary to the belief, it is found that decomposition of ascorbates can be substantially avoided by means of the present invention.

Using the present invention it is found that more than negligible decomposition of ascorbates, such as sodium ascorbates, can be avoided despite heating to temperatures in excess of 100° C., the temperature being less than 180° C.

Thus, it is found that sodium ascorbate heated up to about 100° C. for at least one session of from 2 to 10 minutes, with a cooling interval after each heating cycle, is substantially undecomposed and is not subject to any significant discoloration. The heating preferably is above about 60° C. for at least one 10 minute heating cycle, or at a higher temperature for at least one heating cycle of correspondingly lesser duration. Preferably the heating is to less than 180° C., most preferably substantially less than 180° C., such as not in excess of 130° C. or more preferably 120° C.

It further has been found that the decomposition of ascorbates necessitates the presence of water and oxygen, at least at higher temperatures, and this no doubt is the cause of the loss of Vitamin C from foodstuffs on cooking. It is believed that the mechanism involved is that of dissolved oxygen in the water oxidising the ascorbate to dehydroascorbate. It therefore is highly preferred, at least in performance of the invention in sterilizing an ascorbate, that water, air or both be excluded prior to heating. However, unless air and dissolved oxygen are able to be substantially excluded, it is necessary in sterilizing ascorbates that absolute alcohol, rather than a less expensive azeotropic concentration be used.

A variety of means of heating the biologically affective particulate material can be used. However, heating in a microwave oven or device is particularly preferred, both because of the rapid heating it enables and because of the accurate control over temperature and time.

To establish the chemical stability of biologically affective particulate material when subjected to the sterilising action of ethyl alcohol and heating a series of carefully conducted tests were performed.

Initially a known quantity of sodium ascorbate and 1 ml of ethanol was added to a sterilized IV infusion sample bottle. The sample bottle was then sealed. Routine procedure suggests that the sample bottles be sealed by a rubber insert which is sterilized by heating in a solution of the germicide used in the final product. However, due to the inflammable nature of ethanol, the rubber inserts and aluminium caps were soaked in a "presterilization method" using AR Ethanol for a minimum of 3 days. These pre-tested inserts were plugged in the bottles and the aluminium caps crimped on the top.

The samples were then heated in a microwave oven at full power for 2 to 3 minutes or at lower power for longer periods of time up to 10 minutes, at powder temperatures in excess of 100° C. The resulting amount of "sodium ascorbate" and "sodium ascorbate and dehydroascorbate" were then chemically determined. The results of these tests are shown in Table 1 as follows:

TABLE 1

MEASUREMENT OF SODIUM ASCORBATE AND DEHYDROASCORBATE BEFORE AND AFTER HEATING

| SAMPLE | CHEMICALLY DETERMINED SODIUM ASCORBATE AFTER HEATING GRAMS/BOTTLE | + | CHEMICALLY DETERMINED SODIUM ASCORBATE DEHYDROASCORBATE AFTER HEATING GRAMS/BOTTLE | KNOWN WEIGHT SODIUM ASCORBATE BEFORE HEATING GRAMS/BOTTLE |
|---|---|---|---|---|
| 1 | 15.0 | | 15.0 | 14.7 |
| 2 | 16.0 | | 16.0 | 14.9 |
| 3 | 15.1 | | 15.3 | 14.9 |
| 4 | 15.7 | | 15.8 | 14.9 |
| 5 | 15.1 | | 15.2 | 15.3 |
| 6 | 16.0 | | 16.0 | 14.8 |
| 7 | 16.2 | | 16.3 | 15.2 |
| 8 | 16.3 | | 16.3 | 15.2 |
| 9 | 15.2 | | 15.2 | 15.2 |
| 10 | 15.3 | | 15.4 | 15.1 |
| 11 | 15.4 | | 15.4 | 14.4 |
| 12 | 15.1 | | 15.3 | 15.1 |

From the above it can be seen that no breakdown was observed when the powder was heated as outlined. Further tests on storage of sodium ascorbate and 1 ml Ethanol for periods of up to 1 year at room temperature in a dark cool place also established that this did not affect the chemical composition of the ascorbate.

To establish whether the process of the invention had any adverse effect in respect of contamination (e.g. by possible leaching of heavy metals from the sample bottles or rubber inserts) batches of 3 sample bottles containing 15 grams of ascorbate and 1 ml of ethanol were prepared and analysis for lead, mercury or arsenic were performed before and after heating. The results of these tests are shown in Table 2 as follows:

TABLE 2

ANALYSIS OF SODIUM ASCORBATE FOR LEAD, MERCURY AND ARSENIC CONTENT BEFORE AND AFTER HEAT

| BATCH | TREATMENT CONDITIONS | ARSENIC ug/G = ppm | MERCURY ug/G = ppm | LEAD ug/G = ppm |
|---|---|---|---|---|
| 1 | Heat | <0.02 | <0.02 | <0.2 |
| 2 | Heat | <0.02 | <0.02 | <0.2 |
| 3 | No Heat | <0.02 | <0.02 | <0.2 |

< indicates less than.

These results clearly establish that the method of the invention does not result in any measurable leaching of heavy metals from the bottle or rubber inserts.

Further careful testing has also established that the method of the present invention does not result in any increase in pyrogens in the sample of biologically active particulate material. In fact the results of the tests conducted indicate that the method of the invention causes a decrease in pyrogens.

The present invention shall now be more fully described with reference to the following example. It should be understood however that the example is illustrative only and should not be taken in any way as a restriction on the generality of the invention as described above.

EXAMPLE

Initially 15 g or 30 g of sodium ascorbate were added to sterilized IV infusion sample bottles.

Between 1 million and 50 million organisms (as determined by colony counts) of Staph aureus, Clostridium perfringens, Bacillus subtilus, Candida albicans, Escherichia coli, Clostridium sphenoides and 150 to 30,000 organisms of Penicillium and Asperfillus were added to the 15 grams of sodium ascorbate with or without 1 ml of millipore filtered Ethanol AR. The bottles were then sealed and subjected to a variety of conditions as indicated in Table 3.

Growth or non growth of microorganisms was determined in the following manner:

After the addition of predetermined numbers of microorganisms (by colony counts) to the sodium ascorbate+Ethanol and subsequent+/−heat treatment, the ascorbate was dissolved in 40 mls. of sterile N-saline. One drop was added to each of HBA, NA, McConkeys and Sabarouds medium, under $O_2$ and $AnO_2$ where appropriate, and one drop to Thioglycollate or Todd-Hewitt broth. The broths were subcultured on several subsequent days up to 7 days from the original inoculation and the solid media were examined for up to 7 days from inoculation.

The results of these tests indicated by batches (i.e. 1 batch=at least 6 separate sample bottles) are shown in Table 3 as follows:

TABLE 3

ADDITION OF MICRO-ORGANISMS, TREATMENT AND SUBSEQUENT STERILITY TESTING:

| BATCH | MICRO-ORGANISMS ADDED | TREATMENT CONDITIONS | GROWTH(G) OR NON GROWTH(NG) EXTERNAL QUALITY CONTROL |
|---|---|---|---|
| 1 | b, c, d | No Heat Saline Only | G(All Organisms) |
| 2 | f, g | No Heat Saline Only | G(All Organisms) |
| 3 | b, c, d | No Heat Ascorbate + | G Bacillus Only |

TABLE 3-continued

ADDITION OF MICRO-ORGANISMS, TREATMENT AND SUBSEQUENT STERILITY TESTING:

| BATCH | MICRO-ORGANISMS ADDED | TREATMENT CONDITIONS | GROWTH(G) OR NON GROWTH(NG) EXTERNAL QUALITY CONTROL |
|---|---|---|---|
| 4 | f, g | Ethanol No Heat | NG |
| 5 | b, c, d | Ascorbate + Ethanol No Heat | G Bacillus Only |
| 6 | b, c, d | Ascorbate Only Heat | NG |
| 7 | f, g | Ascorbate + Ethanol Heat | NG |
| 8 | a, b, c, d, e, h | Ascorbate + Ethanol Heat Ascorbate + Ethanol | NG | a *Escherichia coli*
b *staphylococous aureus*
c *Clostridium perfringens*
d *Bacillus subtilus*
e *Candida albicans*
f *Penicillium notatum*
g *Aspergillus niger*
h *Clostridium sphenoides*

As with the method of Australian Pat. specification No. 514503, the invention can be used with materials other than ascorbates. Thus, the invention can be used for sterilizing a variety of combinations of an ascorbate with a variety of pharmaceuticals, or for pharmaceuticals without the presence of an ascorbate.

The product provided by the invention can be used for a variety of applications and using a wide range of containers. In each case, illustrative examples are provided in Australian Pat. specification No. 514503, the disclosure of which is incorporated herein by reference. In general, the product of the invention has the same overall utility as that resulting from the method of Australian Pat. specification No. 514503, but has the additional advantage of being lethal to spore forming organisms, able to survive the use of ethyl alcohol alone. The invention has been found to successfully kill not only Bacillus and Clostridium species but also Penicillium, Aspergillus, Candida, Staph aureus and E. coli.

Finally, it is to be understood that various alterations, modifications and/or additions may be introduced into the constructions and arrangements of parts previously described without departing from the spirit or ambit of the invention.

I claim:

1. A method of sterilizing a biologically affective particulate material selected from the group consisting of ascorbic acid, ascorbic acid salts, and mixtures thereof; said method including the steps of:

(a) adding absolute ethyl alcohol to said biologically affective particulate material; and,
(b) heating said biologically affective particulate material, after said addition of absolute ethyl alcohol, for a sufficient time to kill organisms present, but for less time than would cause substantial breakdown of the particulate material; said heating being at a temperature within the range of about 60° C. to 180° C.

2. A method according to claim 1 wherein the particulate material is sodium ascorbate.

3. A method according to claim 2 wherein approximately 1 ml of absolute ethyl alcohol is added per 15 grams of particulate material.

4. A method according to claim 3 wherein the particulate material and absolute ethyl alcohol are heated to a temperature within the range 100° to 130° C.

5. A method according to claim 3 wherein the absolute ethyl alcohol and particulate material are heated for at least one 10 minute cycle at a temperature above about 60° C.

6. A method according to claim 3 wherein the particulate material is heated for at least one heating cycle of from 2 to 10 minutes with a cooling interval before any successive heating cycle.

7. A method according to claim 1 wherein the absolute ethyl alcohol and particulate material are heated in a microwave oven.

* * * * *